US00PP15959P2

(12) United States Plant Patent
Egger

(10) Patent No.: US PP15,959 P2
(45) Date of Patent: Sep. 13, 2005

(54) ***HEUCHERA* PLANT NAMED 'GYPSY DANCER'**

(50) Latin Name: ***Heuchera* hybrid**
Varietal Denomination: Gypsy Dancer

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 112 days.

(21) Appl. No.: 10/871,805

(22) Filed: Jun. 18, 2004

(51) Int. Cl.[7] ..... A01H 5/00
(52) U.S. Cl. ..... Plt./263
(58) Field of Search ..... Plt./263

(56) References Cited

U.S. PATENT DOCUMENTS

PP11,111 P * 10/1999 Oliver ..... Plt./263
PP12,166 P2 * 10/2001 Heims ..... Plt./263
PP13,215 P2 * 11/2002 Heims ..... Plt./263
PP15,085 P2 * 8/2004 Oliver ..... Plt./263

OTHER PUBLICATIONS http://www.teraanovanurseries.com/pages/plantsH3.html.*
http://www.terranovanurseries.com/news/new_page_3.htm.*

* cited by examiner

*Primary Examiner*—Kent Bell
*Assistant Examiner*—W. C. Haas
(74) *Attorney, Agent, or Firm*—Klarquist Sparkman, LLP

(57) ABSTRACT

A new and distinct hybrid of *Heuchera* plant characterized by small, dark, veiled leaves, light pink flowers, long bloom time, and reblooming habit.

1 Drawing Sheet

Botanical classification: *Heuchera* hybrid.
Variety denomination: 'Gypsy Dancer'.

The present invention relates to a new and distinct cultivar of *Heuchera* hybrid and given the cultivar name of 'Gypsy Dancer'. *Heuchera* is in the family Saxifragaceae. *Heuchera* 'Gypsy Dancer' originated from a cross between H-01-dklf-7, a proprietary, unpatented plant as the seed parent, and H-01-dklf-12, another proprietary, unpatented plant as the pollen parent. Given the characteristics of ornamental foliage and flower form, it is probable that *Heuchera sanguinea, H. micrantha,* and *H. americana* are in the parentage.

This new *Heuchera* is distinguished by:

1. Extremely floriferous. Blooms February to October in the greenhouse in Canby, Oreg. Outside it blooms spring through the summer.
2. Pink flower buds and light pink flowers.
3. Small, slightly wavy, round leaves are dark, veiled silver in the spring and green, veiled silver in the summer.
4. Compact habit.
5. Excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows *Heuchera* 'Gypsy Dancer' growing in a six inch pot in early spring in Canby, Oreg.

DETAILED PLANT DESCRIPTION

The following is a detailed description of the new *Heuchera* cultivar based on observations of a one-and-a-half-year-old specimen grown in six inch container in a cold greenhouse in Canby, Oreg. This greenhouse is kept at between 55 and 85 degrees F. in the summer months and in the winter is heated to frost free, above 32 degrees F. and vented at 55 degrees F. Light intensities are consistent with full sun in Canby, Oreg. which gets 42.8 inches of rain per year and is often cloudy. Plants were hand watered when dry. The color descriptions are all based on The Royal Horticultural Society Colour Chart.

Botanical classification: *Heuchera* hybrid.
Variety denomination: 'Gypsy Dancer'.
Parentage: H-01-dklf-7×H-01-dklf-12 (both proprietary, unpatented plants).

Plant:
- *Form.*—Basal rosette, herbaceous perennial.
- *Hardiness.*—USDA Zone 4 to 9.
- *Vigor.*—Excellent.
- *Roots.*—Fibrous, freely branching, fine, and white in color. Roots develop easily from cuttings.
- *Size.*—14 cm tall from the ground to the top of the foliage and 30 cm wide.
- *Habit.*—Compact, rounded.

Leaf:
- *Type.*—Simple.
- *Arrangement.*—Rosette.
- *Shape.*—Ovate and irregular due to undulations.
- *Lobing/division.*—5 lobes, with 1 to 2 shallow secondary lobes.
- *Venation.*—Palmate.
- *Margins.*—Crenate and undulate.
- *Apex.*—Mucronulate.
- *Base.*—Cordate, lobes strongly overlapping at the base.
- *Blade size.*—5.5 to 8.5 cm long and 4.5 to 7 cm wide.

*Surface texture.*—Thin and leathery, sparsely glandular both sides.

*Petiole size.*—9 to 13 cm. long and 3 mm wide.

*Petiole surface texture.*—Glandular hairs of various sizes.

*Petiole color.*—Greyed Brown 199B.

*Leaf color.*—Spring abaxial — Silver with dark veins. Silver between Black Group 202B and C. Dark veins are between Black 202A and Greyed Purple 187A. Spring abaxial — Red Purple. Between Greyed Purple 187B and Red Purple 59B. Summer adaxial — Silver, edged purple, with green brown veins. Silver between Black Group 202B and C. Dark veins are between Black 202B and Brown 200A. The leaf edges are purple tinged, Red Purple 61A.

Inflorescence:

*Size.*—7 to 12 cm wide and 30 cm deep.

*Type.*—Thyrse.

*Number of flowers.*—120 per thyrse.

*Number of thryse.*—13 in spring flush.

*Peduncle.*—With 0 to 2 petiolate cauline leaves, ovate, 3 to 4.5 cm long and 3 to 3.5 cm wide with a slightly lobed and incised margin. Height — 30 to 60 cm. Diameter — 0.25 cm near base. Surface texture — Hispid.

*Branching.*—3 times. First branch 6.5 cm long at base to 0.9 cm at top. Second branch 1 cm. Third branch 6 to 7 cm. Color — Greyed Purple 187B.

*Pedicel.*—Length — 0.3 to 0.6 cm. Surface texture — Glandular puberulent. Color — Yellow Green 152D.

*Bloom period.*—May through October in Canby, Oreg.

Flower bud:

*Size.*—0.3 cm wide and 0.6 cm long.

*Description.*—Glandular puberulent, ovoid.

*Color.*—Pink. Red Purple 63B at the base and Red Purple 65D at the tip.

Flower:

*Type.*—Perfect, zygomorphic.

*Shape.*—Campanulate.

*Size.*—0.8 cm long and 0.6 cm wide.

*Petal description.*—5 in number, inconspicuous, each spatulate with a clawed base, entire margin, acute apex, White 155D on both surfaces, 0.35 cm long and 0.15 mm wide.

*Calyx.*—5 lobes, ovate, divided ½ way to the base, with glandular hairs, acute apex, 0.8 cm long and 0.6 cm wide.

*Calyx and flower color.*—Light pink. Inside and outside surfaces Red Purple 62B at the base ¼ and White 155B on the lobes (and a faint pink blush), with the outside slightly duller and darker.

*Stamen.*—5 in number, with filaments 4 mm long and White 155A, anthers are also 5 in number, oval, 0.3 mm long and 1.5 mm wide, Orange Red 28A before dehiscence, pollen is Orange 25A and normal in quantity.

*Pistil.*—One with a two-branched stigma, White 155B, typical of the genus, style 0.55 cm. long.

*Fragrance.*—Faint.

*Lastingness.*—Each thryse blooms for about 2 weeks on the plant, reblooming is common.

Fruit:

*Type.*—Two-beaked ovoid capsule.

*Fertility.*—Good.

*Color.*—Brown 200D.

Seed:

*Shape.*—Linear.

*Size.*—2 mm. long.

*Color.*—Black. RHS 202A.

Disease and pest tolerance: Excellent disease resistance to powdery mildew, the common problem of *Heuchera*. Susceptible to root weevils like other *Heuchera*.

COMPARISON TO SIMILAR *HEUCHERAS*

Compared to *Heuchera* 'Vesuvius' (U.S. Plant Pat. No. 13,215), *Heuchera* 'Gypsy Dancer' has a similar habit and size. The foliage of this new cultivar is strongly veiled and not as dark in the summer. The flowers are much larger and lighter pink.

Compared to *Heuchera* 'Veil of Passion' (U.S. Plant Pat. No. 12,166), this new cultivar has shorter flower stalks, longer bloom time, a better veil on the leaves, smaller rounder leaves, and a more compact habit.

Compared to *Heuchera* 'Harmonic Convergence' (U.S. Plant Pat. No. 11,111), this new cultivar has smaller, wavier leaves and flowers that are held further out from the peduncle in a looser arrangement.

I claim:

1. A new and distinct *Heuchera* plant as herein illustrated and described.

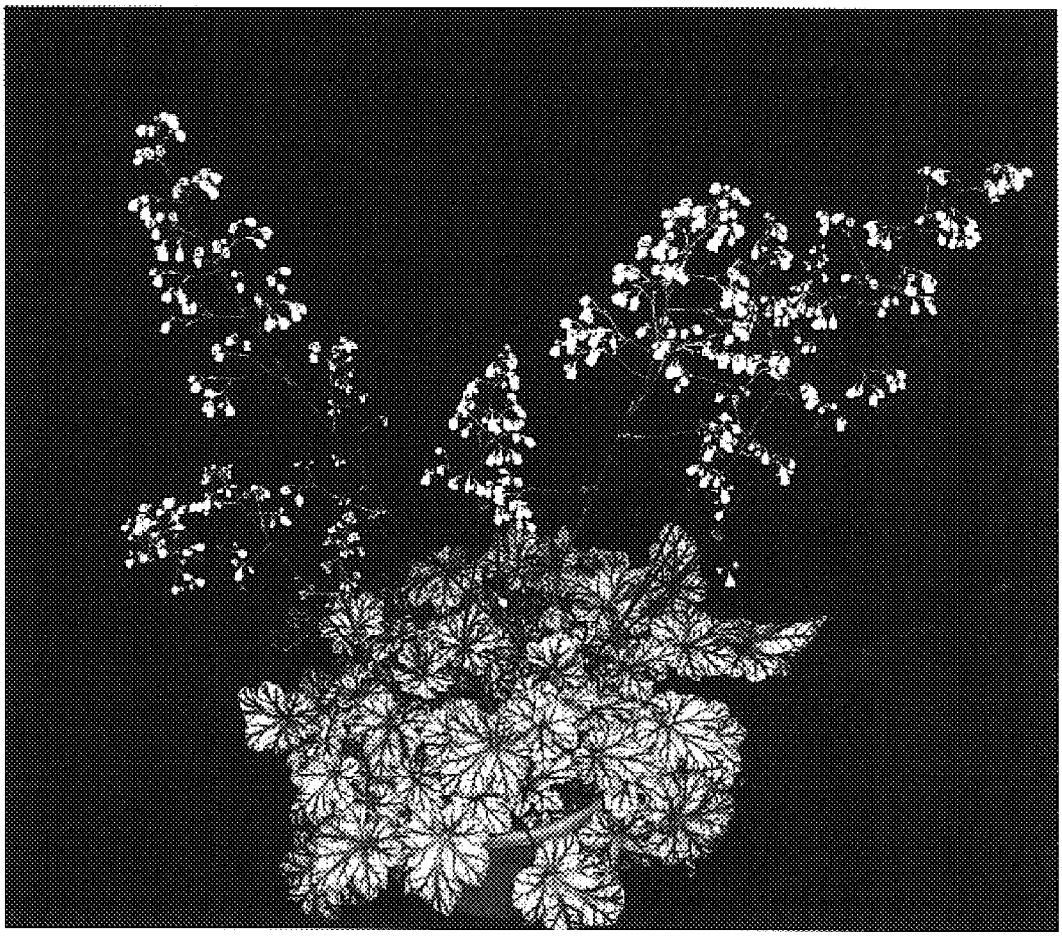

* * * * *